United States Patent
Schulze

(10) Patent No.: US 6,776,782 B2
(45) Date of Patent: Aug. 17, 2004

(54) VESSEL EVERSION INSTRUMENT WITH WIPING ELEMENT

(75) Inventor: Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 378 days.

(21) Appl. No.: 09/891,596

(22) Filed: Jun. 26, 2001

(65) Prior Publication Data

US 2002/0198546 A1 Dec. 26, 2002

(51) Int. Cl.[7] ............................................... A61B 17/04
(52) U.S. Cl. ..................................................... 606/149
(58) Field of Search ................................ 606/149, 205, 606/206, 207, 208, 209, 210, 211, 153, 155, 156, 148, 139; 29/235, 450; 227/19; 81/487, 418

(56) References Cited

U.S. PATENT DOCUMENTS

| | | |
|---|---|---|
| 2,086,371 A | 7/1937 | Tear |
| 2,940,452 A | 6/1960 | Smialowski |
| 3,040,748 A | 6/1962 | Klein et al. |
| 3,057,355 A | 10/1962 | Smialowski et al. |
| 3,180,337 A | 4/1965 | Smialowski |
| 3,506,011 A * | 4/1970 | Silverman .................... 606/149 |
| 3,906,957 A * | 9/1975 | Weston ....................... 606/205 |
| 3,908,662 A | 9/1975 | Razgulov et al. |
| 4,424,811 A * | 1/1984 | Groot ......................... 606/210 |
| 4,470,415 A | 9/1984 | Wozniak |
| 4,494,543 A * | 1/1985 | Hart ........................... 606/211 |
| 4,622,970 A | 11/1986 | Wozniak |
| 5,014,407 A * | 5/1991 | Boughten et al. ............. 29/235 |
| 5,047,046 A * | 9/1991 | Bodoia ....................... 606/205 |
| 5,849,012 A * | 12/1998 | Abboudi ..................... 606/205 |
| 5,957,938 A * | 9/1999 | Zhu et al. ................... 606/149 |
| 5,976,161 A * | 11/1999 | Kirsch et al. ............... 606/149 |
| 6,273,902 B1 * | 8/2001 | Fogarty et al. ............. 606/207 |

* cited by examiner

Primary Examiner—A. Vanatta

(57) ABSTRACT

An instrument for everting an end of a vessel. The instrument has a frame and a mandrel having a distal end and a proximal end. The mandrel is mounted to the frame and axially movable. The distal end of the mandrel is insertable into the lumen of a vessel. A first wiping element and an opposed second wiping element are mounted to the frame with the mandrel positioned therebetween. The first and second wiping elements are laterally movable from a spaced-apart position to a closed position.

14 Claims, 4 Drawing Sheets

VESSEL EVERSION INSTRUMENT WITH WIPING ELEMENT

FIELD OF THE INVENTION

The field of art to which this invention relates is medical devices, more specifically, medical devices and surgical procedures for performing anastomosis of hollow organs such as blood vessels.

BACKGROUND OF THE INVENTION

Anastomotic surgical procedures are common in the field of cardiac surgery. These procedures are conventionally used for repairing a damaged or diseased blood vessel. In a typical anastomotic procedure, a surgeon joins a first blood vessel to a second blood vessel and creates a passageway between the two blood vessels to provide for the communication of blood flow. For this kind of anastomosis, the surgeon typically uses specialized grasping tools to manipulate a tiny, curved needle attached to an extremely fine surgical filament (e.g., under 0.001 inch diameter) to suture the vessels together. The vessels may be joined end-to-end, end-to-side, or side-to-side. To facilitate healing of the joined vessels, the prevailing standard of care requires that the surgeon suture the inside surfaces of the first and second vessels together, intima to intima. The surgeon must take great care not to damage the intima of each vessel so that endothelial cells may form over the anastomosis without the formation of thrombus or other complications, thus improving the likelihood of a long term patency of the vessels. For life-saving procedures such as coronary artery bypass graft surgery (CABG), this is especially important. When performing a distal anastomosis in a conventional CABG procedure, the surgeon typically sutures an end-to-side anastomosis of a distal end of a graft vessel (such as a segment of saphenous vein harvested from the patient) to a side of a target vessel (the stenosed coronary artery). For a proximal anastomosis in a conventional CABG procedure, the surgeon sutures a proximal end of the graft vessel to the side of the aorta.

As this field of art has progressed over the last several years, new anastomotic methods have been developed and introduced in attempts to replace the suturing technique briefly described above. Many of these methods incorporate novel fasteners and fastener appliers. The requirement, however, to maintain intima-to-intima contact of the joined vessels remains just as important with these approaches. In fact it is often necessary, prior to joining the vessels, for the surgeon to evert (i.e., turn inside out) the end of at least one of the vessels over the end of a member such as a tube, ferrule, or bushing, etc., which is a component of the fastener or fastener applier. This exposes the intima of that vessel for presentation to the intima of the other vessel prior to fastening the vessels.

Although it is possible to evert larger vessels (over 5 mm in diameter) using standard forceps and graspers available in the operating room, such methods are slow and may result in excessive damage to the vessel everted. And, often the surgeon requires assistance in performing the eversion procedure. Furthermore, vessels smaller than 5 mm are very difficult, if not impossible, to evert using such methods.

There are several requirements for an effective vessel eversion device. As noted earlier, for proper healing, it is important not to injure the intima of either vessel during the eversion procedure. The eversion device also must be easy for the surgeon to use without assistance and require only a few steps to operate. The eversion device must be useful for a wide range of blood vessel sizes, particularly small vessels, e.g., having a diameter of about 2–3 mm or less. In addition, it is desirable for the eversion device to be useful on one end of a vessel, when the opposite end is already attached to the patient (e.g., at the distal anastomosis of a patient undergoing a CABG procedure). The eversion device should also allow for the proper length of everted tissue, depending upon the requirements of the anastomosis device or method to be used. Finally, it is desirable that the eversion device be low cost and yet operate reliably.

Accordingly, there is a need in this art for novel devices and methods for engaging and everting the end of a blood vessel (or other tubular body organ), which can be used in a quick and effective manner without causing trauma to the vessel or the intima of the vessel (or tubular body organ).

SUMMARY OF THE INVENTION

It is an object of the present invention to provide novel eversion devices which are easy for the surgeon to use without assistance, and which efficiently and effectively engage blood vessels and evert the ends of blood vessels, including blood vessels having small or fine diameters.

A further object of the present invention is to provide novel eversion devices which engage blood vessels and evert the ends of blood vessels without causing trauma to the blood vessel or the intima of the blood vessels.

It is yet another object of the present invention to provide novel methods of engaging and everting blood vessels quickly and efficiently, while preventing or minimizing damage to the blood vessels and the intimas of the blood vessels.

It is still yet a further object of the present invention to provide a novel vessel eversion device and procedure for everting one end of a vessel having the other end already attached to another vessel.

Accordingly, an eversion instrument for everting an end of a vessel is disclosed. The instrument has a frame. There is a mandrel having a distal end and a proximal end. The mandrel is mounted to the frame and axially movable. The distal end of the mandrel being insertable into a lumen of a vessel. A first wiping element having a first wiping face and an opposed second wiping element having a second wiping face are mounted to the frame with the mandrel positioned therebetween. The first and second wiping elements are laterally movable from a spaced-apart position to a closed position.

Yet another aspect of the present invention is a method of everting a vessel. In this method, a tubular workpiece is provided. The tubular workpiece has a tube member having an inner lumen, an inner surface, an outer surface, a distal end, and a proximal end. An instrument for everting an end of a vessel over an end of a tubular workpiece is also provided. The instrument has a frame. There is a mandrel. The mandrel has a distal end and a proximal end. The mandrel is mounted to the frame and axially movable with respect thereto. The distal end of the mandrel is insertable into a lumen of a vessel. The instrument has a first wiping element having a first wiping face and an opposed second wiping element having a second wiping face. The first and second wiping elements mounted to the frame with the mandrel positioned therebetween. The first and second wiping elements being laterally movable from a spaced-apart position to a closed position. The mandrel is inserted into a lumen of a vessel for holding the vessel inside of the lumen of the tubular workpiece. Then, the first and second wiping elements are closed over the mandrel proximal to the end of the vessel. Next, the first and second wiping surfaces of said first and second wiping elements are wiped along the mandrel in the distal direction and over the tubular workpiece, thereby everting the end of the vessel over the distal end of the tubular workpiece.

Yet another aspect of the present invention is a system for everting a vessel. The system consists of the combination of the above-described evers ion instrument and tubular workpiece.

These and other aspects and advantages of the instruments and methods of the present invention will become more apparent from the following description and accompanying drawings.

DETAILED DESCRIPTION OF THE INVENTION

Figure 1:
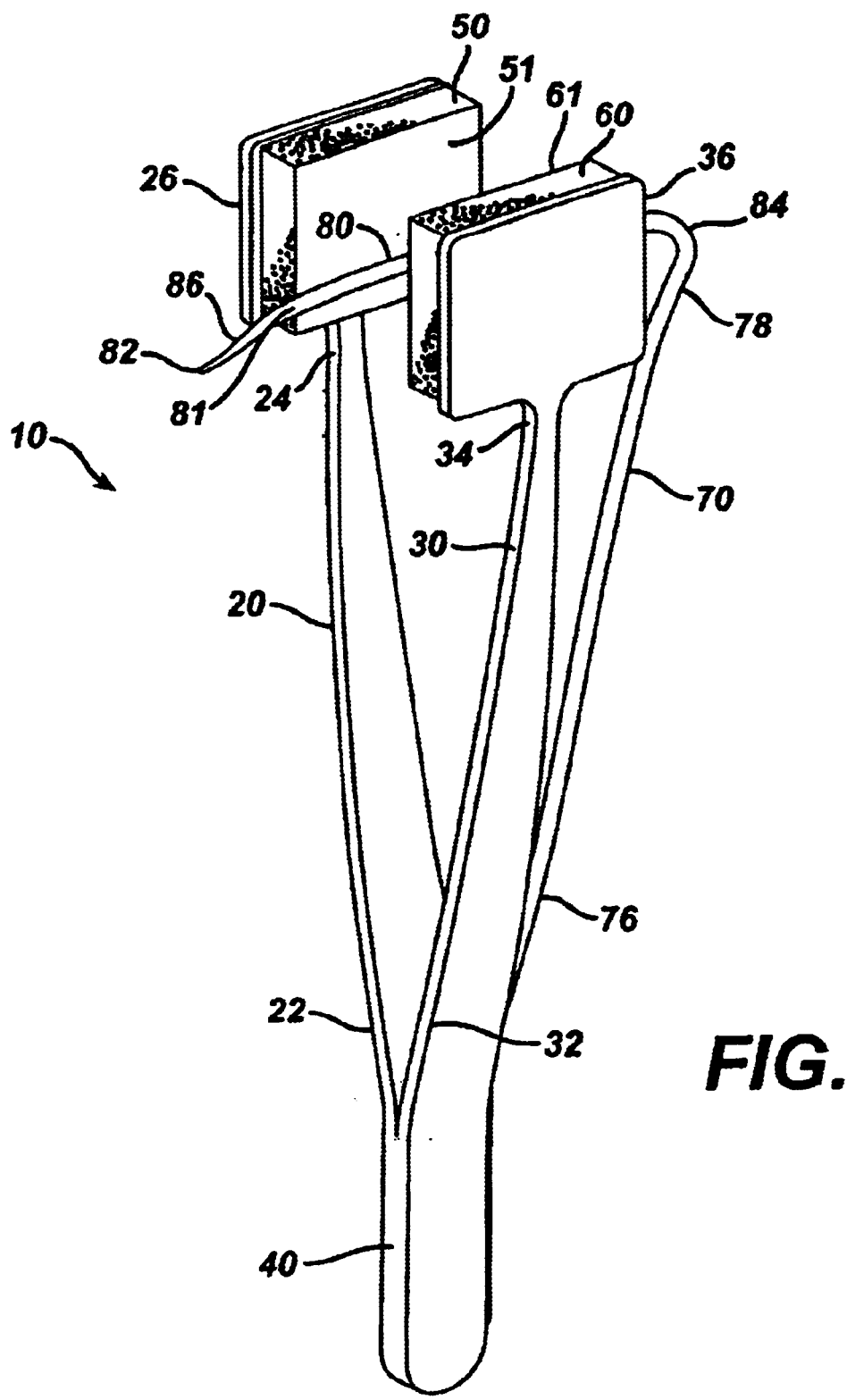
FIG. 1 is a perspective view of an eversion instrument 10 of the present invention.

The vessel eversion instrument of the present invention is illustrated in FIGS. 1–8. Referring first to FIG. 1, an eversion instrument 10 for everting an end 105 of a vessel is illustrated. Typically, the distal end 105 of the vessel 100 is everted using the instruments 10 and methods of the present invention, however, it is possible to also evert the proximal ends as well. A surgeon or an assistant may use eversion instrument 10, for example, for everting an end of a harvested segment of the greater saphenous vein prior to its anastomosis to a coronary artery during a CABG procedure. Eversion instrument 10 is sized and constructed in order to be held and operated with a single hand. Eversion instrument 10 is seen to have a first arm 20, an opposing, second arm 30, and a centrally mounted, spring arm 70. First arm 20 is seen to have member 28 having proximal end 22 and distal end 24. A proximal end 22 of first arm 20 is joined to a proximal end 32 of second arm 30, thus forming a handle 40. The distal end 24 of first arm 20 attaches to a first paddle member 26. The distal end 34 of second arm 30 attaches to a second paddle member 36, so that first and second paddle members, 26 and 36, are substantially opposite each other. First arm 20 and second arm 30 are preferably made of a stiff but spring-like material such as a semi-hardened stainless steel or a polycarbonate plastic, for example, so that first paddle member 26 and second paddle member 36 are normally sprung apart as shown in FIG. 1. Spring arm 70 is relatively slender compared to first and second arms, 26 and 36, and is made of a spring-like material such as a semi-hardened stainless steel or a rigid, flexible plastic such as high density polyethylene. Spring arm 70 has a proximal end 76 attached at handle 40 between first and second arms, 26 and 36 and a distal end 78. The proximal end 84 of a mandrel 80 is mounted to distal end 78 such that mandrel 80 is positioned between first and second paddles, 26 and 36. Mandrel 80 is seen to have a curved portion 86 that tapers to a distal tip 82. Mandrel 80 is seen to have exterior surface 81. Mandrel 80 is slender for insertion into the lumen of a vessel having an internal diameter approximately in the range of 3–5 mm. Mandrel 80 is made of a resiliently stiff biocompatible material such as, for example, high density polyethylene, so that when mandrel 80 is inserted into a rigid wall tube having an internal diameter approximately in the range of 3–5 mm, curved portion 86 of mandrel 80 is at least partially straightened. In the embodiment of the present invention shown in FIG. 1, mandrel 80 is an extension of spring arm 70. Eversion instrument 10 is further seen to have a first wiping element 50 mounted on first paddle member 26 and a second wiping element 60 mounted on second paddle member 36. First wiping element 50 is seen to have a wiping surface 51, and second wiping element 60 is seen to have a wiping surface 61. First and second wiping elements, 50 and 60, may be made of any one of a number of resilient, soft materials such as the following, although not limited to these materials: foam rubber, cloth, cotton gauze pads, multi-layers of facial tissues, plastic bag pouches sealed with enclosed air or gel, and low durometer elastomers such as latex rubber. First wiping element 50 is mounted to first paddle 26 and second wiping element 60 is mounted to second paddle 36 preferably with an adhesive, although numerous other conventional attachment methods will be apparent to those skilled in the art, including mechanical fasteners, welding, friction fits, etc. and the like and equivalents thereof. When an operator squeezes together first arm 20 and second arm 30 such that arms 20 and 30 are moved to a position closer to each other, first wiping element 50 and second wiping element 60 come together with the surfaces 51 and 61 substantially in contact with each other and with exterior surface 81 of mandrel 80, wherein mandrel 80 is located in-between, and with a force proportional to the squeezing force applied by the operator.

Figure 2:
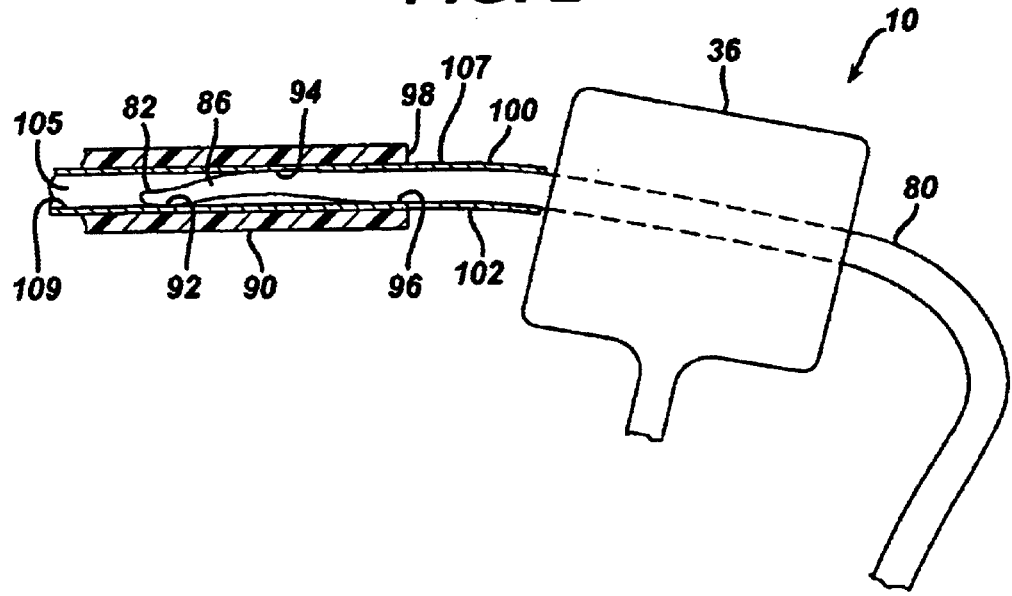
FIG. 2 is a partial side view of the distal end of the eversion instrument 10 of FIG. 1, showing a first step of the operational sequence for everting a vessel 100 held in a tube 90.

The steps for the method of use of eversion instrument 10 are now described according to the operational sequence depicted in FIGS. 2 through 7. Referring initially to FIG. 2, the first step of the operational sequence is inserting mandrel 80 into a vessel 100 that is held in a tube 90. Vessel 100 may be a portion of the greater saphenous vein harvested from a surgical patient, as already noted, or also may be a portion of another blood vessel or hollow organ in the body. Vessel 100 is seen to have distal end 102, interior lumen 105, exterior surface 107 and interior surface 109. Tube 90 may be a bushing, ferrule, anastomotic coupler, or a portion of an anastomotic fastener applier or delivery device, for example. Tube 90 is seen to have lumen 91, exterior surface 99, interior surface 93, and distal end 98. During the steps of the operational sequence, the operator, an assistant, or a holding device holds tube 90. The operator inserts vessel 100 into the lumen of tube 90 so that a distal vessel portion 102 of vessel 100 extends beyond an open distal end 98 of tube 90. The length of distal vessel portion 102 may vary depending on the requirements of the particular anastomostic technique associated with tube 90, and will be sufficient to provide for an effective eversion, but generally the length of distal vessel portion 102 is approximately in the range of 5–15 mm. During this first step the operator may squeeze together first paddle 26 member (see FIG. 1) and second paddle member 36 in order to facilitate insertion of distal tip 82 of mandrel 80 into lumen 105 of vessel 100. Curved portion 86 of mandrel 80 partially straightens during insertion into lumen 105 of vessel 100, which is constrained within the lumen 91 of tube 90, establishing a first contact 92, a second contact 94, and a third contact 96, between the exterior surface 81 of mandrel 80 and the interior surface 109 of vessel 100. Because mandrel 80 is made of flexibly resilient material, mandrel 80 straightens easily during insertion into vessel 100, yet has sufficient spring-back to provide a gentle holding force on vessel 100 against the interior surface 109 of tube 90, thus helping to prevent vessel 100 from receding further into tube 90 during the next steps of the operational sequence. Also, because spring arm 70 easily bends when force is applied to mandrel 80, the allowable insertion force of mandrel 80 into vessel 100 is limited, thus helping to prevent injury to vessel 100. The operator inserts mandrel 80 into vessel 100 at least far enough, to establish first, second, and third contact points, 92, 94, and 96.

Figure 3:
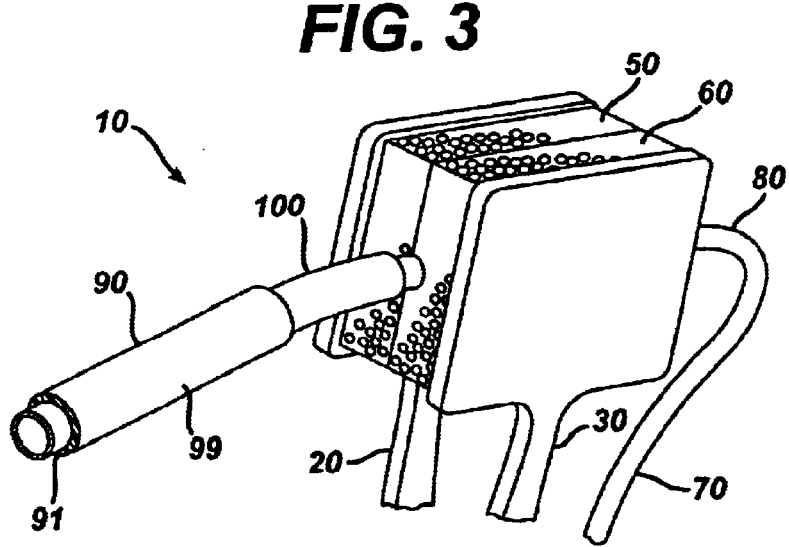
FIG. 3 is a perspective view of the distal end of eversion instrument 10, again showing the first step of the operational sequence for everting vessel 100 held in tube 90.

FIG. 3 is a perspective view of a portion of eversion instrument 10 for the first step of the operational sequence shown also in FIG. 2. Mandrel 80, attached to spring arm 70, is shown inserted into vessel 100, which is held in tube 90. The operator squeezes together first arm 20 and second arm 30, bringing first wiping element 50 and second wiping element 60 together in a closed position around mandrel 80.

Figure 4:
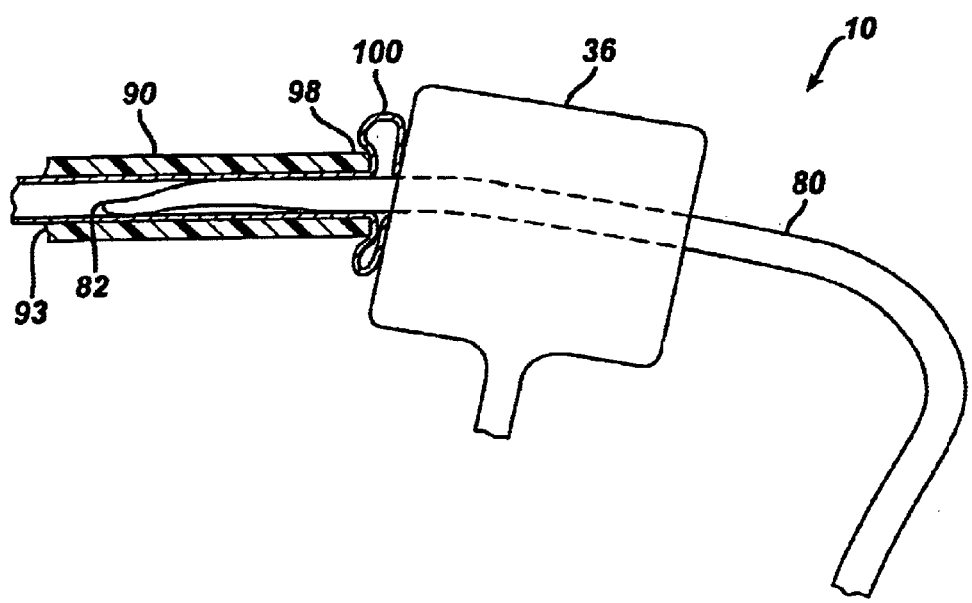
FIG. 4 is a side view of the distal end of eversion instrument 10, showing a second step of the operational sequence for everting vessel 100, wherein the distal vessel end 102 begins to evert over the distal end of tube 90.
Figure 5:
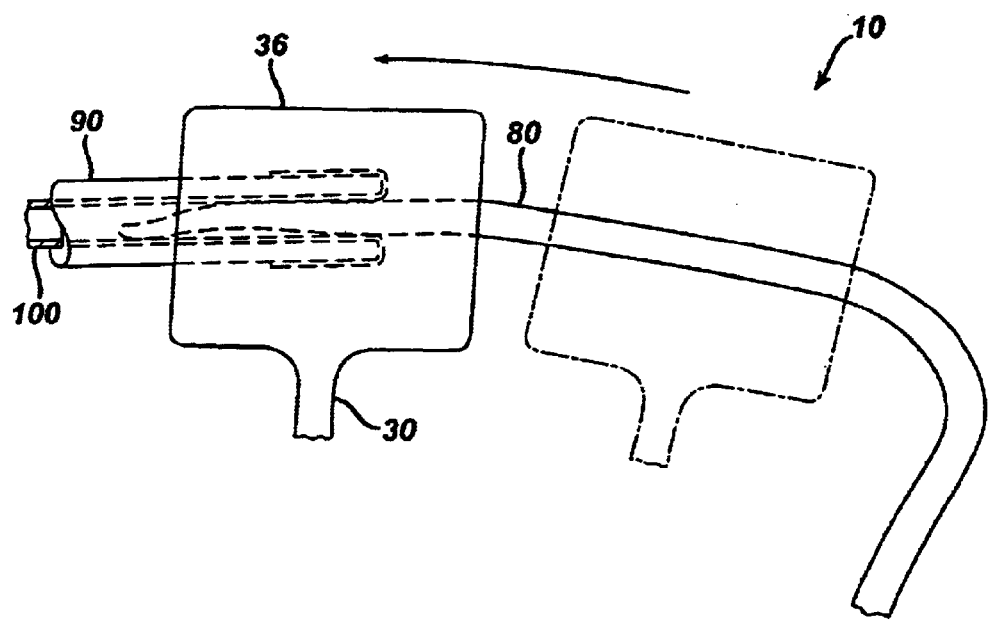
FIG. 5 is a side view of the distal end of eversion instrument 10, showing a third step of the operational sequence for everting vessel 100, wherein distal vessel end 102 is seen to be everted.

Now referring to FIGS. 4 and 5, a second step of the operational sequence is the eversion of end 102 of vessel 100. The operator holds together first paddle 26 (see FIG. 1) and second paddle 36 while advancing them towards tube 90. Consequently, the surfaces 51 and 61 of first wiping element 50 and second wiping element 60 (see FIG. 3) wipe along mandrel 80 and cause end 102 of vessel 100 to "accordion" or gather as shown in FIG. 4. During this second step, distal tip 82 of mandrel 80 may move slightly further into the lumen of tube 90, without adverse consequence. The operator continues this wiping motion of first and second paddles, 26 (hidden) and 36, as shown in FIG. 5 in order to completely evert end 102 of vessel 100 over the end 98 of tube 90 and onto tube exterior surface 99.

Figure 6:
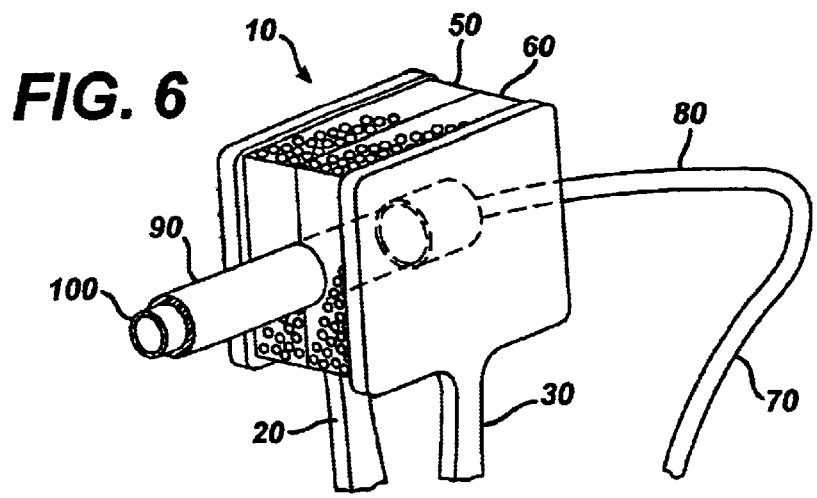
FIG. 6 is a perspective view of the distal end of eversion instrument 10, again showing the third step of the operational sequence for everting vessel 100, wherein distal vessel end 102 is everted.

FIG. 6 is a perspective view of a portion of eversion instrument 10, showing the completion of step 2 also shown in FIG. 5. In FIG. 6, first wiping element 50 and second wiping element 60 are shown conforming around the outside of tube 90 and everted vessel end 102 while first arm 20 and second arm 30 are held together. Mandrel 80 remains inside of vessel 100, but spring arm 70 deflects, thus preventing the operator from inadvertently forcing mandrel 80 further into lumen 105 of vessel 100 and possibly injuring vessel 100.

Figure 7:
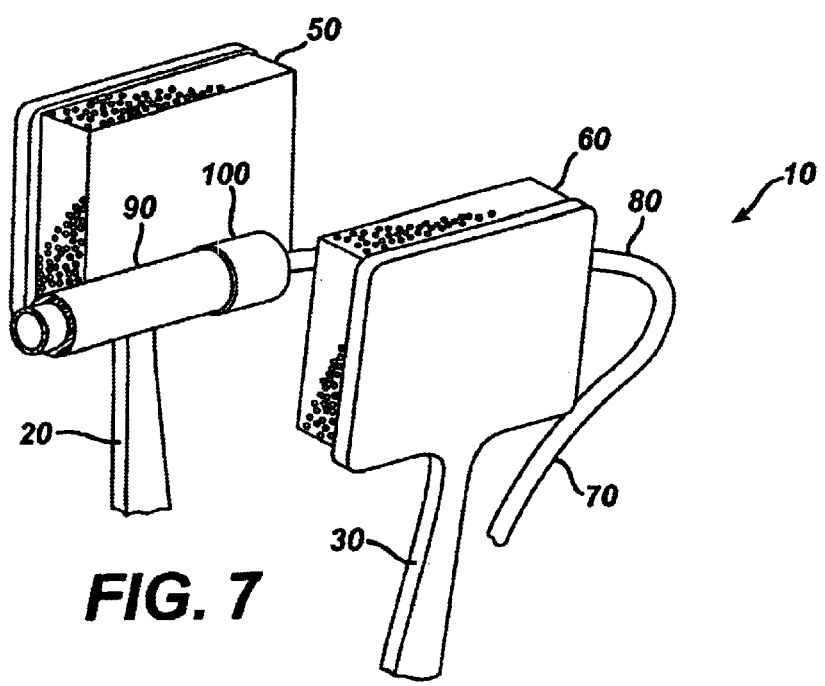
FIG. 7 is a perspective view of the distal end of eversion instrument 10, showing a fourth step of the operational sequence for everting vessel 100.
Figure 8:
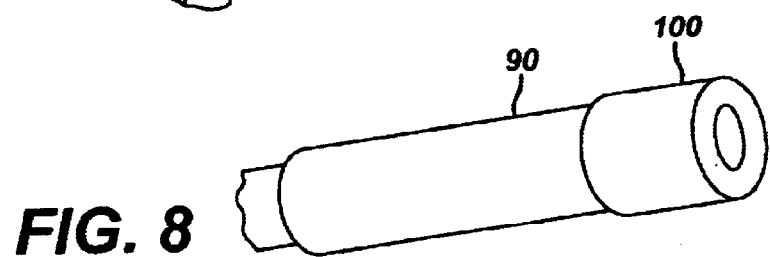
FIG. 8 is a perspective view illustrating distal vessel end 102 of vessel 100 everted over the distal end of tube 90.

FIG. 7 shows a third step of the operational sequence. The operator releases first arm 20 and second arm 30 to allow first wiping element 50 and second wiping element 60 to move to a spaced apart position. If vessel 100 is not properly everted over the end 98 of tube 90, the operator may repeat the second and third steps shown in FIGS. 4–7. The operator may initially apply only a very light squeezing force to first and second arms, 20 and 30, to minimize trauma to vessel 100, gradually increasing this force with each subsequent wiping motion. The operator then withdraws mandrel 80 from vessel 100, pulling back on spring arm 70 if necessary. FIG. 8 is a perspective view of vessel 100 everted over tube 90, after mandrel 80 has been removed.

Those skilled in the art will envision other types of handles and arms than the present embodiment for positioning wiping elements 50 and 60 as described herein. Furthermore, wiping elements 50 and 60 may be disposable and detachable from eversion instrument 10 for quick and easy replacement during a surgical procedure, or for resterilization of the handle and use on another patient.

The following example is illustrative of the principles and practice of the present invention, although not limited thereto.

EXAMPLE

A patient undergoing cardiac coronary artery bypass graft (CABG) surgery is prepared for surgery and anesthetized in a conventional manner in accordance with the prevailing medical standards. The patient's chest is opened in a conventional manner by cutting through the sternum and expanding the rib cage with a conventional surgical retractor instrument. The patient's heart is accessed in a conventional manner and the patient is connected to a pulmonary bypass machine and the heart is stopped. A section of the patient's saphenous vein, which has already been harvested by this time, is prepared for use as a graft vessel. The graft vessel end that is to be attached to the aorta for the proximal anastomosis is everted using an eversion instrument of the present invention as already described in the detailed description and shown in FIGS. 2–6. In FIG. 6, vessel 80 is shown everted over tube 90. One embodiment of tube 90 is disclosed in published patent application WO0056228, "Low Profile Anastomosis Connector", filed on Mar. 20, 2000, assigned to By-Pass, Inc., and which is hereby incorporated herein by reference. As described in WO0056228, a metallic anastomosis connector comprising a plurality of ring segments is used to fasten the graft vessel to another vessel such as the aorta. The distal end of the graft vessel is then be anastomotically attached to a coronary artery on the heart using a conventional hand suturing method. Additional bypasses are performed in the same manner or variations, depending on the patient's condition and anatomy. The remainder of the CABG procedure is conducted in a conventional manner and includes the steps of inspecting and repairing the grafts for leaks, checking blood flow, removing the patient from the pulmonary bypass machine, and closing the surgical incision.

The eversion instruments and eversion methods of the present invention have many advantages. The present invention is less traumatic to the intima of the vessel during the eversion procedure than conventional surgical graspers and the like. The present invention is easy for the surgeon to use without assistance and requires only a few steps to operate. The present invention is useful for a wide range of blood vessel sizes, particularly small vessels, e.g., having a diameter of about 2–3 mm or less. In addition, the present invention is useful on one end of a vessel, when the opposite end is already attached to the patient (e.g., at the distal anastomosis of a patient undergoing a CABG procedure). The present invention also allows for the proper length of everted tissue over the tube, bushing, or the like, depending on the requirements of the anastomosis device or method being used. Finally, the present invention may be manufactured inexpensively.

Accordingly, there is a need in this art for novel devices and methods for engaging and everting the end of a blood vessel (or other tubular body organ) over a member such as a tube, ferrule, bushing, or the like which can be used in a quick and effective manner without causing trauma to the vessel or the intima of the vessel (or tubular body organ).

Although this invention has been shown and described with respect to detailed embodiments thereof, it will be understood by those skilled in the art that various changes in form and detail thereof may be made without departing from the spirit and scope of the claimed invention.

What is claimed is:

1. An instrument for everting an end of a vessel over an end of a tubular workpiece, said instrument comprising
    a frame;
    a mandrel having a distal end and a proximal end, said mandrel mounted to said frame and axially movable, said distal end being insertable into a lumen of a vessel;
    a first wiping element having a first wiping face and an opposed second wiping element having a second wiping face, said first and second wiping elements mounted to said frame with said mandrel positioned therebetween, said first and second wiping elements laterally movable from a spaced-apart position to a closed position.

2. The instrument of claim 1, wherein said frame comprises a forceps having a first arm and a second arm, said first arm having a distal end and a proximal end, said second arm having a distal end and a proximal end, said proximal ends of said first and second arms attached together, said first wiping element attached to said distal end of said first arm, said second wiping element attached to said distal end of said second arm such that the first and second wiping faces are substantially opposed to each other, said wiping elements normally in said spaced-apart position, said first and second arms manually movable to position said first and second wiping elements to said closed position.

3. The instrument of claim 1 further comprising a mandrel spring mounted to the frame, wherein the proximal end of the mandrel is mounted to the mandrel spring and wherein said mandrel is biased by said mandrel spring so that said distal end of said mandrel is distal to said first and second wiping elements.

4. The instrument of claim 1, wherein said first and second wiping elements comprise a soft and resilient material.

5. The instrument of claim 1, wherein said first and second wiping elements are removeably attached to said frame.

6. The instrument of claim 1, wherein said proximal end of said mandrel has a first diameter and the distal end of said mandrel has a second diameter smaller than said first diameter, and said mandrel is curved between said proximal and distal ends, so that said mandrel is insertable to a predetermined depth within the bore of a workpiece, and said mandrel holds the vessel at three regions of contact against an interior bore surface of said workpiece.

7. The instrument of claim 1, wherein said mandrel is made from a flexible material.

8. A method for everting a vessel over the end of a tubular workpiece, said method comprising the steps of:
    providing a tubular workpiece comprising a tube having an inner lumen, an inner surface, an outer surface, a distal end, and a proximal end;
    providing an instrument for everting an end of a vessel over an end of a tubular workpiece, said instrument comprising
        a frame;
        a mandrel having a distal end and a proximal end, said mandrel mounted to said frame and axially movable, said distal end being insertable into a lumen of a vessel;
        a first wiping element having a first wiping face and an opposed second wiping element having a second wiping face, said first and second wiping elements mounted to said frame with said mandrel positioned therebetween, said first and second wiping elements laterally movable from a spaced-apart position to a closed position;
    inserting said mandrel into a lumen of a vessel for holding the vessel inside of the lumen of the tubular workpiece;
    closing said first and second wiping elements over said mandrel proximal to the end of the vessel;
    wiping said first and second wiping surfaces of said first and second wiping elements along said mandrel in the distal direction and over the tubular workpiece, thereby everting the end of the vessel over the distal end of the tubular workpiece.

9. The method of claim 8 further comprising the steps of opening the first and second wiping elements and withdrawing the mandrel from the lumen of the vessel.

10. A system for everting a vessel, comprising:
    the combination of
        I. a tubular work piece comprising a tube having an inner lumen, an inner surface, an outer surface, a distal end, and a proximal end; and,
        II. an instrument for everting an end of a vessel over an end of a tubular workpiece, said instrument comprising
            a frame;
            a mandrel having a distal end and a proximal end, said mandrel mounted to said frame and axially movable, said distal end being insertable into a lumen of a vessel;
            a first wiping element having a first wiping face and an opposed second wiping element having a second wiping face, said first and second wiping elements mounted to said frame with said mandrel positioned therebetween, said first and second wiping elements laterally movable from a spaced-apart position to a closed position.

11. The system of claim 10, wherein said frame comprises a forceps having a first arm and a second arm, said first arm having a distal end and a proximal end, said second arm having a distal end and a proximal end, said proximal ends of said first and second arms attached together, said first wiping element attached to said distal end of said first arm, said second wiping element attached to said distal end of said second arm such that the first and second wiping faces are substantially opposed to each other, said wiping elements normally in said spaced-apart position, said first and second arms manually movable to position said first and second wiping elements to said closed position.

12. The system of claim 10 further comprising a mandrel spring mounted to the frame, wherein the proximal end of the mandrel is mounted to the mandrel spring and wherein said mandrel is biased by said mandrel spring so that said distal end of said mandrel is distal to said first and second wiping elements.

13. The system of claim 10, wherein said first and second wiping elements comprise a soft and resilient material.

14. The system of claim 10, wherein said first and second wiping elements are removeably attached to said frame.

* * * * *